United States Patent [19]
Ankeny et al.

[11] Patent Number: 4,884,436
[45] Date of Patent: Dec. 5, 1989

[54] AUTOMATED TENSION INFILTROMETER

[75] Inventors: Mark D. Ankeny; Thomas C. Kaspar; Robert Horton, Jr., all of Ames, Iowa

[73] Assignee: Iowa State University Research Foundation, Inc., Ames, Iowa

[21] Appl. No.: 260,022

[22] Filed: Oct. 20, 1988

[51] Int. Cl.$^4$ ............................................. G01N 15/08
[52] U.S. Cl. ........................................... 73/38; 73/73
[58] Field of Search ...................................... 73/38, 73

[56] References Cited

U.S. PATENT DOCUMENTS

| | | | |
|---|---|---|---|
| 2,540,096 | 2/1951 | Bull | 73/38 |
| 3,103,117 | 9/1963 | Richards | 73/73 |
| 3,871,211 | 3/1975 | Tal | 73/73 |
| 3,884,067 | 5/1975 | Mottes | 73/73 |
| 3,898,872 | 8/1975 | Skaling et al. | 73/73 |
| 3,910,300 | 10/1975 | Tal | 73/73 X |
| 4,478,069 | 10/1984 | Zuckerwar | 73/38 |
| 4,520,657 | 6/1985 | Marthaler | 73/38 X |

OTHER PUBLICATIONS

Moore, Burch and Wallbrink, "Preferential Flow and Hydraulic Conductivity of Forest Soils," *Soil Sci. Soc. Am. J.*, pp. 876–881, vol. 50, 1986.

Constantz and Murphy, "An Automated Technique for Flow Measurements from Mariotte Reservoirs," *Soil Sci. Soc., Am. J.*, pp. 252–254, vol. 51, 1987.

Clothier and White, "Measurement of Sorptivity and Soil Water Diffusivity in the Field," *Soil Sci. Soc. Am. J.*, pp. 241–244, vol. 45, 1981.

*Primary Examiner*—Stewart J. Levy
*Assistant Examiner*—Joseph W. Roskos
*Attorney, Agent, or Firm*—Zarley, McKee, Thomite, Voorhees & Sease

[57] ABSTRACT

An automated tension infiltrometer including a soil contacting base to which is mounted a porous plate for interfacing the infiltrometer with the soil to be analyzed. A Marriotte column is positioned in the base so that its open bottom end abuts the porous plate. A bubble tower is also positioned in the base and has a bubbling tube operatively connected between its interior and interior of the Marriotte column. The bubble tower is adjustable to provide variable tension to the Marriotte column. First and second transducers are positioned at the upper and lower parts of the Marriotte column and continuously measure pressure changes at those positions while water from the column infiltrates into the soil. By correlating these measurements, improved precision in measuring water level is achieved, which in turn allows improved results regarding deriving soil characteristic information.

13 Claims, 1 Drawing Sheet

U.S. Patent    Dec. 5, 1989    4,884,436
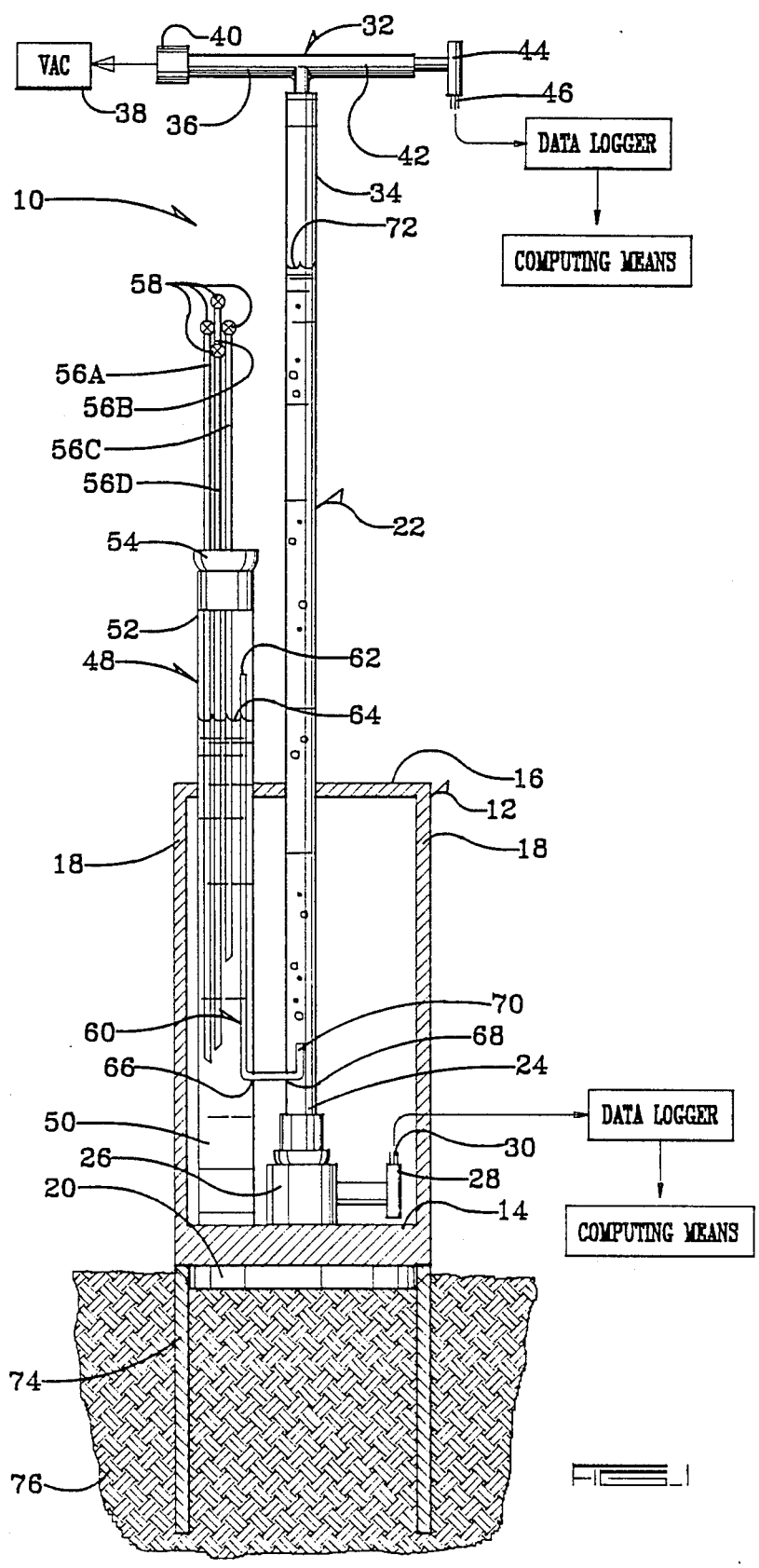

AUTOMATED TENSION INFILTROMETER

BACKGROUND OF THE INVENTION a. Field of the Invention

The present invention pertains to devices for analyzing hydraulic characteristics of soil, and in particular, to an infiltrometer for automatically measuring water infiltration under tension.

b. Problems in the Art

Infiltrometers have been utilized for a number of years to attempt to derive soil characteristics. For example, an elementary infiltrometer is disclosed in "Measurement of Sorptivity in Soil Water Diffusivity in the Field" by Clothier and White, SOIL SCI. SOC. AM. J., Vol. 45, 1981, pgs. 241–245. The fundamental theory and structure of infiltrometers is described in this article, and it is incorporated by reference herein.

Infiltrometers have been found useful to measure soil characteristics and properties such as sorptivity, unsaturated hydraulic conductivity, and macroporosity, to name a few examples. Such measurements help derive information which is useful in determining characteristics such as soil hydraulic properties for studying leeching and erosion, modeling soil pore structure to estimate drainage and other characteristics, and allowing prediction of such things as root growth and other associated factors.

The type of infiltrometer portrayed in Clothier and Wilson is elementary and does have certain weaknesses and problems. For example, truly accurate and reliable measurement is difficult. The production of tension in the reservoir is many times erratic and measurement ranges are many times insufficient to be very useful, especially at low flow rates and low tensions.

Attempts have been made to improve upon these elementary infiltrometers. For example, as disclosed in Constantz and Murphy, "An Automated Technique For Flow Measurements From Marriotte Reservoirs" SOIL SCI. SOC. AM. J., Vol. 51, 1987, pgs. 252–254, incorporated by reference herein, one such attempt is described. Additionally, that article also describes the problems with other types of infiltrometer systems.

The Constantz and Murphy technique utilizes a pressure transducer at the top of the Marriotte column. Continuous pressure readings can be converted into changes in water level to derive the relevant measurements needed. This technique does have certain problems however.

First of all, there is room for improvement with regard to reliability of the data from this type of system. The bubbling action still creates erratic results affecting readings of the transducer. Especially at low flow rates and tension, these measurements must be very precise over the test periods. With only one transducer, a significant measurement error can exist due to tension fluctuations or "noise" caused by bubbling in the Marriotte column.

Such problems also impact upon how quickly the data can be obtained, and with respect to the ease of obtaining the relevant data. Of course, the better and more reliable the measurements, the better and more reliable the derivation of results regarding soil characteristics.

The present state of the art also has problems with regard to the flexibility of such testing systems. For example, there is room for improvement in whether and how tension can be varied in the Marriotte column. It is also advantageous to have a device which allows interchangeability of Marriotte columns.

It is therefore a principal object of the present invention to provide an automated tension infiltrometer which improves over or solves the deficiencies and problems in the art. A further object of the present invention is to provide an infiltrometer as above described which facilitates automated measurement of infiltration.

A further object of the present invention is to provide an infiltrometer as above described which allows easy and flexible interfacing with recording instrumentation and computing components to allow quick and reliable derivation of results for soil characteristics.

Another object of the present invention is to provide a means as above described which improves reliability and accuracy of measurements.

A still further object of the present invention is to provide a means as above described which is accurate and reliable even at low tensions and low flow rates.

A further object of the present invention is to provide a means as above described which can obtain more data than conventional systems.

Another object of the present invention is to provide a means as above described which can obtain measurements more quickly than conventional systems.

A further object of the present invention is to provide a means as above described which can be adjusted to operate reliably over a range of tensions.

A further object of the present invention is to provide a means and method as above described which allows interchangeability of components, such as Marriotte columns.

A further object of the present invention is to provide a means as above described which is efficient, convenient to use, and economical.

These and other objects, features, and advantages of the present invention will become more apparent with reference to the accompanying specification and claims.

SUMMARY OF THE INVENTION

The present invention comprises an automated tension infiltrometer for deriving information regarding soil characteristics. A Marriotte column and a bubble tower are positioned and secured within a base member. The bubble tower has means to control tension in the Marriotte column and communicates with the Marriotte column through a bubble tube that extends between them.

The Marriotte column has a bottom open end which abuts against a porous plate means, which in turn is used as the interface between the Marriotte column and the soil being tested. The plate is also removably secured into the base.

In operation, the Marriotte column is substantially filled with fluid, usually water. An upper pressure transducer is operatively connected to the Marriotte column to continuously monitor pressure at the uppermost end of the Marriotte column. A lower pressure transducer does the same thing at the bottom of the Marriotte column.

Air can be evacuated from the upper end of the Marriotte column. The bubble tube can be operated to set tension in the Marriotte column. Pressure readings are then taken as water infiltrates from the Marriotte column into the soil. From the changes in pressure recorded from the upper and lower transducers, the level of water in the Marriotte column can be continuously and accurately measured, and various soil characteristics can then be derived from the measurements.

As an enhancement, the automated tension infiltrometer can be operatively connected to control means such as a computer so that its operation and readings from the transducers can be completely automated. Alternatively, the readings from the transducers can be simply communicated to a data logger means to record the measurements. The bubble tower can be manually operated.

The Marriotte columns can be interchanged to provide different length and diameter Marriotte columns.

BRIEF DESCRIPTION OF THE DRAWINGS

FIG. 1 is a front elevational view of a preferred embodiment of the invention with a base for the instrument and the soil shown in cross-section.

DETAILED DESCRIPTION OF THE PREFERRED EMBODIMENT

In order to aid in an understanding of the invention, a preferred embodiment will now be described in detail. This description will be made with reference to FIG. 1. Reference numerals will be used to identify various components of the preferred embodiment.

Automated tension infiltrometer 10 shown in FIG. 1 includes the following components. A base 12 has a lower end 14 and upper end 16 with sidewalls 18. Base 12 consists essentially of a hollow housing to which other components can be mounted.

A porous plate assembly 20 is mounted in lower end 14 of base 12. In the preferred embodiment, porous plate assembly 20 is used to interface infiltrometer with the soil and allow fluid to pass through at a controlled rate. It can consist of fine mesh nylon filter abutting an acrylic face plate which has numerous aperatures through it. This combination is then mounted into plate assembly 20 with sealing rings and/or gaskets. Other arrangements and materials can be used to accomplish this function.

An elongated Marriotte column, such as are well-known in the art, is mounted in the base 12, extending from the bottom open end 24, which abuts porous plate assembly 20, through base 12 and out its upper end 16. In the preferred embodiment, bottom end 24 of Marriott column 22 is interfaced with porous plate assembly 20 by a connection means 26 which is a basically cylindrical tubular member. Connection means 26 also holds a lower or bottom pressure transducer 28 which has appropriate electrical connections 30 for electrical communication to recording instrumentation.

A manifold 32 is attached to upper end 34 of Marriotte column 22, which is also open. Manifold 32 is basically a t-shaped tubular means, with the first branch 36 connectible to a negative pressure source 38 via septum 40. The second branch 42 of manifold 32 communicates with an upper or top pressure transducer 44 which also has appropriate electrical connections 46 for communication to an electrical recording means.

A bubble tower 48 is also mounted in base 12. Bottom end 50 of bubble tower 48 is closed and rests against porous plate assembly 20 or is secured in the lower end 14 of base 12. It extends parallelly and adjacent to Marriotte column 22 out of the upper end 16 of base 12. Its upper end 52 is sealed by stopper 54.

A plurality of tubes 56 a, b, c, and d, extend through stopper 54 between the exterior of bubble tower 48 and its interior. Each tube 56 a–d is of a different length and has a lower end which extends to a different depth inside bubble tower 48. The upper ends of tubes 56 a–d each have a separate valve 58 which can be opened or closed according to desire; that is singly or in combinations.

Bubble tube 60 has a first end 62 which is positioned in the upper portion of bubble tower 48 (above fluid line 64) and then extends downwardly a distance through bubble tower 48, exits aperture 68 in the side of bubble tower 48 into aperture 68 of Marriotte column 22 and terminates in an open second end 70 beneath fluid line 72 in Marriotte column 22. Bubble tube 60 is sealed around its perimeter at aperture 66 and 68 to prevent any fluid leakage.

FIG. 1 also shows that in the preferred embodiment, a tubular boot 74 can surround the lower portion of the porous plate assembly 20 and be used to isolate a segment of soil 76 which is desired to be tested, and prevent fluid from diffusing laterally from beneath porous plate assembly 20. This is an optional component and is not necessary for the operation of the invention.

It is to be understood that in the preferred embodiment, Marriotte columns of different sizes and lengths can be interchanged according to desire. It has been found that measurement precision is dependent upon the diameter of the Marriotte column. At low flow rates, it is preferred to use a small diameter column rather than a large diameter column because it results in a greater change in height per unit inflow and in improved measurement precision.

Marriotte column 22 is generically described as a water reservoir and is preferred to be transparent and of a constant diameter tubing. In the preferred embodiment, a range of inside diameter (i.d.) Marriotte columns can be used, for example 6.4, 12.7, and 19.0 millimeter i.d. columns. It has been found that columns of less than 6.4 millimeter i.d. are problematic in that trapped air pockets form below the water surface during bubbling. However, smaller columns could be used if bubble size is reduced by using a smaller-diameter bubbling tube 60 at the air entry point in Marriotte column 22.

Bubbling tube 60 in the preferred embodiment is 1.6 millimeter (mm) i.d. polypropolyne tubing. The inner wall of Marriotte column 22 is coated with Sigmacote, of Sigma Chemical Company, to reduce water beading which could decrease measurement precision.

Negative pressure source 38 can be any vaccuum source such as a vaccuum pump or the like. Upper and lower pressure transducers 44 and 28 are series PX-136 4-wire full-bridge (0–5 PSI gauge type) pressure transducers available from Omega Engineering with appropriate calibrations, transducers 44 and 28 output a linear voltage as a function of tension ($r^2 > 0.999$). It is to be understood that upper pressure transducer 44 is mounted in the headspace above fluid line 72 in Marriotte column 22, whereas bottom or lower pressure transducer 28 is mounted near the base of Marriotte column 22, in the preferred embodiment approximately 60 mm above the surface of soil 76. Both transducers 44 and 28 are electrically connected by wires 46 and 32 to appropriate electronic recording means. In the preferred embodiment this is a data logger 78 programmed to record paired readings of transducers 44 and 28 at regular intervals. In the preferred embodiment, the data logger can be a Campbell 21X data logger available from Campbell Scientific Incorporated. A computing means 80 can be connected to at least data logger(s) 78 to receive and operate upon the readings.

Bubble tower 48 utilizes tubes 56 a–d, which act as air entry ports. Tubes 56 a–d and valves 58 can be opened or closed individually or in various combinations and control tension in Marriotte column 22 by allowing air entry through tubes 56 a–d at different distances below fluid line 64 of bubble tower 48. Valves 58 can be preset to tensions from 0.02 to 0.50 m (meters). Valves 58 are used to switch from one port to another.

Utilizing this arrangement, it has been found, by monitoring tension at rapid infiltration rates ($>5\times10^{-4}$ms$^{-1}$), that air flow through bubbling tube 60 is sufficient to limit the flow-induced tension increase at the surface of soil 76 to $<5$ mm of water above that imposed by bubble tower 48.

With regard to the preferred embodiment of porous plate assembly 20, the fine mesh nylon filter can be a broadcloth-covered Spex 400-mesh nylon filter (air entry value of about 250 mm of water). This filter will directly contact soil 76. Finer filters must be used for greater tension. The face plate backing the filter can be a circular 8.9 centimeter (cm) diameter acrylic face plate which has been grooved on a lathe and has approximately are 2 mm hole per 10 mm$^2$ area, to allow relatively unimpeded water flow. The face plate can then be glued to a 8.25 cm i.d. acrylic ring that seats in a gasket at the bottom of base 12 of infiltrometer 10. Using this arrangement, the resulting infiltration surface has a diameter of 8.25 cm.

The infiltrometer of the preferred embodiment is useful for a range of water tensions from 0.02 to 0.50 m and for infiltration rates of $1\times10^{-8}$ to $5\times10^{-4}$ms$^{-1}$. As is well known, infiltration rates are calculated from the change in water height in Marriotte column 22. Water height in the present invention is automatically measured by using the difference in tension between upper and lower pressure transducers 44 and 28. The precision of water height measurement using two transducers (SD=2.2 mm) is increased as compared to height measurements made with only one transducer (SD=6.2 mm), which introduces substantial measurement error due to tension fluctuations or "noise" caused by bubbling in the Marriotte column.

Bubble tower 48 is utilized for tension regulation, and interchangeability of Marriotte columns 22 of different diameters is used to match column volume with expected cumulative infiltration. This assists in reaching the objectives of the invention, including quick and accurate tension control even at low tensions, improved measurement precision even at low flow rates, and automatic measurement and data collection, which increases measurement speed and eliminates bubbling-induced variability.

The invention is particularly useful at low tension and low flow rates. It is also very advantageous because it is well suited for large numbers of measurements and for ranges of tensions, which is required for most field studies.

Operation of the infiltrometer 10 of FIG. 1 can be as follows. Water is filled into Marriotte column 22 and bubble tower 48. Negative pressure 38 is operated to evacuate air from the top of Marriotte column 22. As air is evacuated, tension gradually increases and pulls bubbles from the second end 70 of bubble tube 60. As this occurs, tension decreases rapidly. A cyclical rise and fall of tension as bubbles are formed and released results. These tension changes are continuously measured by upper pressure transducer 44. The bottom transducer 28 simultaneously measures the same tension fluctuations.

Infiltrometer 10 determines water height in Marriotte column 22 from these tension measurements. Tension fluctuation in Marriotte column 22 is proportional to the surface tension of the water-air interface in bubbling tube 60 and to the change in bubble radius as it expands and breaks free from bubbling tube 60. Larger bubbles result in increased tension variation.

By simultaneously measuring tension at the to and bottom of Marriotte column 22, the difference in tension between upper and lower transducers 44 and 28 is less variable than data from a top transducer alone. In other words, bubble-induced tension fluctuations registered at both top and bottom transducers 44 and 28 cancel out when the two values are subtracted. Consequently, the difference in tension between the two transducers is dependent only upon height of water column and not upon bubble size or tension at a given instant.

Because bubble-induced tension variations may not cancel out for all measurements, it has been determined that it is important to time the paired data readings of the two transducers per bubbling interval to somewhere around 0.25 pairs s$^{-1}$ to 5 pairs s$^{-1}$. This would result in about twenty paired data readings per bubbling interval. However, reading frequency can be varied outside of this range.

It is to be understood that utilizing the present invention, the standard deviation of the two transducer data set can be reduced nearly tenfold relative to a single transducer data set. Utilization of two transducers also nearly eliminates the need for autocorrelation analysis.

The included preferred embodiment is given by way of example only, and not by way of limitation to the invention, which is solely described by the claims herein. Variations obvious to one skilled in the art will be included within the invention defined by the claims.

For example, it is to be understood that instead of having two transducers, namely upper pressure transducer 44 and lower pressure transducer 28, with measurements being correlated between the two, a differential pressure transducer can be used. A first part of the differential pressure transducer would be operatively connected to the head space of upper end 34 Marriotte column 22, and a second port operatively connected near bottom end 24 Marriotte column 22, essentially where upper and lower transducers 44 and 28 are positioned as described earlier. Using this arrangement, the bubbling "error" could be cancelled physically by the differential pressure transducer instead of mathematically. Thus, it is understood that the full use of equivalents may be resorted to without departing from the spirit or scope of the invention.

What is claimed is:

1. An automated tension infiltrometer comprising:
   a soil contacting base;
   a liquid permeable, porous plate means secured to the base for interfacing the infiltrometer with soil to be tested;
   a Marriotte column means for providing a source of constant hydraulic pressure secured to the base and having an open bottom end abutting the plate means;
   bubble tower means secured to the base including a bubble tube means extending into the Marriotte column means for providing bubbles of adjustable volume, size, and frequency to the Marriotte column means to set tension in the Marriotte column means;

upper transducer means for monitoring the pressure at the top of the Marriotte column means;

lower transducer means for monitoring the pressure at the lower end of the Marriotte column means, the monitoring of pressure at the upper and lower transducer means allowing various soil characteristics to be obtained.

2. The infiltrometer of claim 1 wherein the porous plate means includes a fine mesh filter for contacting the soil.

3. The infiltrometer of claim 1 including connection means, the marriotte column means being interchangeable in the connection means to allow various inside-diameter sized Marriotte column means to be utilized.

4. The infiltrometer of claim 1 wherein the bubble tower means comprises a tubular column with a closed bottom end, a stopper means in an open upper end, and a plurality of tubes extending to different depths inside the bubble tower means, each tube having an upper end extended outside the bubble tower means to which is operatively connected a valve means for allowing opening and closing of air passage through any tube, singly on in combination, to adjust the amount of air provided the Marriotte column means.

5. The infiltrometer of claim 4 wherein the bubble tube means extends from above a fluid line in the bubble tower means to below a fluid line in the Marriotte column means.

6. The infiltrometer of claim 5 wherein opening of one or more of valve means for the plurality of tubes in the bubble tower means variably controls tension in the Marriotte column means.

7. The infiltrometer of claim 1 wherein the upper and lower transducer means are separate transducers each having electrical connection means to a correlating recording device for recording measurements of the transducer means.

8. The infiltrometer of claim 1 wherein the upper and lower transducer means comprise upper and lower ports for a differential pressure transducer which measures differences of pressure at upper and lower positions of the Marriotte column means and outputs a signal representing such pressure differential.

9. The infiltrometer of claim 1 further comprising data logger means for receiving measurements from the upper and lower transducer means and for recording those measurements.

10. The infiltrometer of claim 9 further comprising computing means connected to the data logger means for processing the measurements to derive soil characteristics information.

11. An automated tension infiltrometer comprising:
a soil contacting base;
a liquid permeable, porous plate means secured to the base for interfacing the infiltrometer with soil to be tested;
a Marriotte column means for providing a source of constant hydraulic pressure secured to the base and having an open bottom end abutting the plate means;
bubble tower means secured to the base including a bubble tube means extending into the Marriotte column means, the bubble tower means controlling tension in the Marriotte column means;
differential pressure transducer means having a first port operatively connected to the top of the Marriotte column means for monitoring pressure at the top of the Marriotte column means, and having a lower port operatively connected to the bottom of the Marriott column means for monitoring pressure at the bottom of the Marriotte column means, the differential pressure transducer outputting a signal representing the difference of pressure between the top and bottom of the Marriotte column means.

12. A method of automated tension measurement in an infiltrometer comprising:
positioning a Marriotte column means for providing a source of constant hydraulic pressure having a porous plate means for interfacing the infiltrometer with soil to be tested covering a bottom open end of the Marriotte column in abutment to the soil to be tested;
filling the Marriotte column means to a preselected level with a fluid;
evacuating air from the upper end of the Marriotte column means;
controlling tension in the Marriotte column means;
simultaneously measuring pressure at the top and bottom of the Marriotte column means during infiltration of fluid from the Marriotte column means into the soil.

13. The method of claim 12 further comprising controlling tension in the Marriotte column means by a bubble tower means having variable tension control.

* * * * *